US006457363B1

(12) United States Patent
Schafer (10) Patent No.: US 6,457,363 B1
(45) Date of Patent: Oct. 1, 2002

(54) METHOD AND APPARATUS FOR DETECTING AND CHARACTERIZING SPLITS IN LOGS

(75) Inventor: Mark E. Schafer, Ambler, PA (US)

(73) Assignee: Perceptron, Inc., Plymouth, MI (US)

( * ) Notice: Subject to any disclaimer, the term of this patent is extended or adjusted under 35 U.S.C. 154(b) by 0 days.

(21) Appl. No.: 09/882,446

(22) Filed: Jun. 15, 2001

Related U.S. Application Data (62) Division of application No. 09/197,165, filed on Nov. 20, 1998, now Pat. No. 6,295,907.
(60) Provisional application No. 60/082,018, filed on Apr. 16, 1998.

(51) Int. Cl.$^7$ ............................................... G01N 29/04
(52) U.S. Cl. ........................................................ 73/596
(58) Field of Search .............................. 73/579, 596–600, 73/620, 624–632

(56) References Cited

U.S. PATENT DOCUMENTS

| | | | |
|---|---|---|---|
| 3,664,180 A | 5/1972 | McDonald et al. | 73/67.7 |
| 4,356,850 A | 11/1982 | Halgrimson et al. | 144/357 |
| 4,523,468 A | 6/1985 | Derkacs et al. | 73/598 |
| 4,571,999 A | 2/1986 | Arita et al. | 73/598 |
| 4,831,545 A | 5/1989 | Floyd et al. | 144/356 X |
| 4,838,085 A | 6/1989 | Pellerin et al. | 73/597 |
| 4,858,469 A | 8/1989 | Hosgood et al. | 73/579 |
| 4,879,659 A | 11/1989 | Bowlin et al. | 144/357 X |
| 4,984,172 A | 1/1991 | Luminari | 144/356 X |
| 5,007,291 A | 4/1991 | Walters et al. | 73/640 |
| 5,024,091 A | 6/1991 | Pellerin et al. | 73/597 |
| 5,097,881 A | 3/1992 | Mack | 144/356 |
| 5,237,870 A | 8/1993 | Fry et al. | 73/588 |
| 5,307,679 A | 5/1994 | Ross | 73/597 |
| 5,396,799 A | 3/1995 | Ross et al. | 73/579 |
| 5,435,361 A | 7/1995 | Knerr | 144/357 X |
| 5,538,056 A | 7/1996 | Thoma | 144/357 X |
| 5,631,424 A | 5/1997 | Nieters et al. | 73/598 |
| 5,760,308 A | 6/1998 | Beall et al. | 73/644 |
| 5,804,728 A | 9/1998 | Beall et al. | 73/598 |
| 6,295,907 B1 | 10/2001 | Schafer et al. | 83/75.5 |

FOREIGN PATENT DOCUMENTS

JP        435841        2/1992 ..................... 83/72

Primary Examiner—Richard A. Moller
(74) Attorney, Agent, or Firm—Woodcock Washburn LLP (57) ABSTRACT

Ultrasonic techniques are applied to the measurement of wooden members to detect splitting during sawing operations and thereby allow modification of a sawing technique or change in saw cut placement.

21 Claims, 7 Drawing Sheets

METHOD AND APPARATUS FOR DETECTING AND CHARACTERIZING SPLITS IN LOGS

CROSS-REFERENCE TO RELATED APPLICATIONS

This application is based on provisional application 60/082,018 filed Apr. 16, 1998 of the same name and hereby incorporated by reference. Also, this application is a divisional of application Ser. No. 09/197,165, filed Nov. 20, 1998.

STATEMENT REGARDING FEDERALLY SPONSORED RESEARCH OR DEVELOPMENT

This invention was supported in part by funds from the U.S. Government (98-CRADA-3162) and the U.S. Government may therefore have certain rights in the invention.

BACKGROUND OF THE INVENTION

The present invention relates to an apparatus for the detection of splits in logs and other wooden members, and specifically to an apparatus employing ultrasonic energy to detect and characterize such splits. The wooden members may be trees, logs, beams, planks, lumber, boards or wood composites and the like.

When logs are sawn to size in the field using commercial harvesters, they are often subject to the creation of splits when cut. This is because one end of the log is unsupported during the cutting operation. Splits also occur when the tree is initially felled. The splits are undesirable, introduce defects in the lumber that is sawn from the logs, and thereby reduce the value of the log itself. A recent examination of the problem indicates that up to 70% of logs harvested in this manner contain splits. If the problem is detected in the field at the time of sawing, then either the operator can modify his/her practice to reduce this incidence, or the logs can be cut longer such that sufficient material will remain free of defects. In other words, if a 12 foot long clear log is desired, and the harvester detects end splits for a distance of 12 inches, then the next cut will be made so as to have the required 12 feet after the defective portion is removed.

Traditionally identification of defects and other features affecting lumber grade has been performed visually, for example, by a saw operator visually inspecting the log or board prior to determining the necessary cross or rip cuts that will yield the best product output or yield. Recently a number of electronic scanning systems have been produced using cameras and lasers to automate this visual process. Such optical techniques are limited to the detection of superficial defects in the wooden members and even these techniques may be defeated by dirt, bark, stain or other markings on the outside of the log. More importantly, internal defects such as splits are generally not visible.

What is needed is an apparatus for detecting and characterizing splits internal to a wooden member, that is also robust against the harsh environment of a typical lumber operation or the like and that is safer, less costly and more compact than instruments based on x-rays or other electromagnetic radiation.

SUMMARY OF THE INVENTION

The present inventors have discovered that splits create an acoustic discontinuity that may be detected by an ultrasonic signal transmitted through the wooden member across the grain at a number of different angles around the perimeter of the wooden member and comparing the received waveforms. Even after the splits have closed and are no longer visible, they create an acoustic discontinuity that may be detected. Detection of the splits may be used to control the operation of a saw to change cut locations or to modify the sawing technique.

Specifically, the present invention provides an apparatus for detecting splits in wooden members using at least one pair of opposed ultrasonic transducers positioned to contact the wooden members on opposed points along an axis across a grain of the wooden member. Driving circuitry drives one of the ultrasonic transducers so as to produce an ultrasonic wave of known characteristics and detection circuitry connected to an other of the ultrasonic transducers receives the ultrasonic wave after passage through the wooden member to provide a measurement. The wooden member measurement is repeated along axes at a plurality of angles about the outer perimeter of the wooden member across the grain of the wooden members, and an electronic computer communicating with the driving and detection circuits executes a stored program to compare the wooden member measurements at the plurality of angles to detect a split in the wooden member indicated by variation in the measurements.

Thus it is one object of the invention to provide a simple and inexpensive method of detecting splits in wooden members.

Multiple pairs of ultrasonic transducers may be each positioned to transmit and receive an ultrasonic wave along different circumferential angles or may use a movable carriage holding at least one pair of ultrasonic transducers and movable about the wooden member to position the ultrasonic transducers at the plurality of angles.

Thus it is another object of the invention to permit flexibility in selecting between electrical scanning employing multiple transducers or mechanical scanning employing a single or limited number of pairs of transducers.

The comparison performed by the apparatus may address the attenuation of total energy in the received ultrasonic wave, the change in spectral energy distribution in the received ultrasonic wave, the spreading of the temporal distribution of energy in the received ultrasonic wave, phase distortion in the received ultrasonic wave or combinations of the above.

Thus it is another object of the invention to provide for a multiparameter measurement so as to improve the accuracy and robustness of the ultrasonic measurements.

The apparatus may include a means for measuring the thickness of the wooden members along the axis and may calculate a time of flight of the ultrasonic wave between transducers to determine a sound velocity, or may determine a change in energy or phase as a function of thickness.

Thus it is another object of the invention to account for other factors affecting the received ultrasonic waveform so as to improve the ability of the apparatus to detect localized defects or other features within wooden members of varying thickness and type.

The apparatus may include a means for moving the wooden members with respect to the ultrasonic transducers perpendicular to the axis of the transducers and the output of the electronic computer may be a measure of wooden members' quality as a function of position.

Thus it is another object of the invention to determine the length of splits for the purpose of guiding a cutting of the wooden member to optimize its usage.

The foregoing and other objects and advantages of the invention will appear from the following description. In the description, reference is made to the accompanying drawings which form a part hereof and in which there is shown by way of illustration a preferred embodiment of the invention. Such embodiment does not necessarily represent the full scope of the invention, however, and reference must be made to the claims herein for interpreting the scope of the invention.

DETAILED DESCRIPTION OF THE INVENTION

Figure 1:
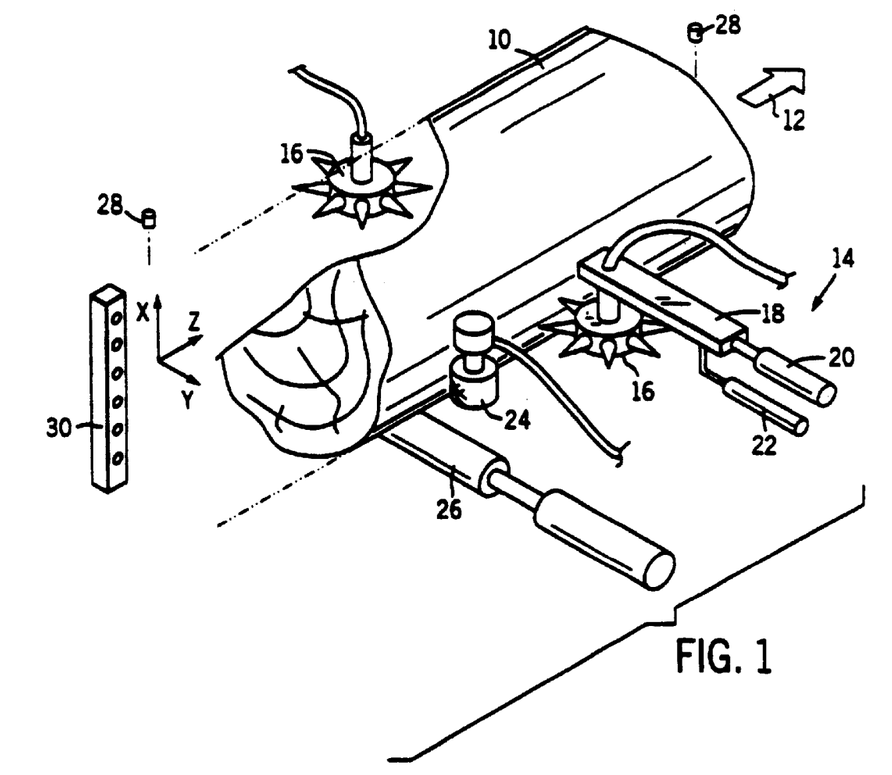
FIG. 1 is a perspective view in partial cutaway of a wooden member as may be moved in a translation direction with respect to opposed ultrasonic transducers incorporated into wheels and pressed against the opposed sides of the wooden member, FIG. 1 further showing other sensing devices for characterizing the wooden members' shape and position.

In FIG. 1, a wooden member 10 such as a log is shown positioned horizontally so that its grain direction and axis define a z-axis of a Cartesian coordinate system with the x-axis directed generally upward and the y-axis horizontal. As will be understood from the following description, the term wooden member should be held to embrace trees, logs, lumber, boards and wood composites in various stages of processing.

The wooden member 10 may be moved in a translation direction 12 with respect to a measurement assembly 14 by one or more driven rollers 26 that support the wooden member 10 from underneath. In some instances (not shown here), the wooden member may be rotated.

The measurement assembly 14 includes a first (transmitting) and second (receiving) ultrasonic transducer 16 encased in rollers such as may roll against the surface of the wooden member 10 as it moves in the translation direction 12. The ultrasonic transducers 16 are opposed along the y-axis to transmit and receive an ultrasonic signal through the wooden member 10 radially and perpendicular to the grain, and are attached to slide assemblies 18 (only one shown) which are biased toward the wooden member 10 by an air cylinder 20 or the like. The wheels of the transducers 16 thereby maintain contact with the outer surface of the wooden member 10 while being free to rotate about their axes.

A linear position sensor 22 may be attached to the slide assembly 18 so as to provide a measurement of the separation of the transducers 16 and hence a measurement of the width of the wooden member 10 along the axis between the transducers 16. An encoder/roller assembly 24 positioned against the outer surface of the wooden member 10 provides a measurement of the z-axis position of the wooden member 10 as it moves in the translation direction 12. Auxiliary sensors, such as photoelectric proximity sensors 28, may be positioned separately along the z-axis and directed downward along the x-axis to detect the beginning and end of the wooden member 10 as it moves, and thus to provide a measurement of its length. A sensor array 30 having multiple photoelectric sensors arrayed along the x-axis may provide a height measurement of the wooden member 10 along the x-axis to further characterize the wooden member 10.

Ultrasonic transducers encased in a wheel and suitable for use in this application with regular wooden members such a boards and logs stripped of bark, are commercially available from James Instruments of Chicago, Ill. (Model C-7219) and Dapco Industries of Ridgefield, Conn. The transducers may be oriented to produce either longitudinal or shear waves through the wooden member 10.

Figure 15:
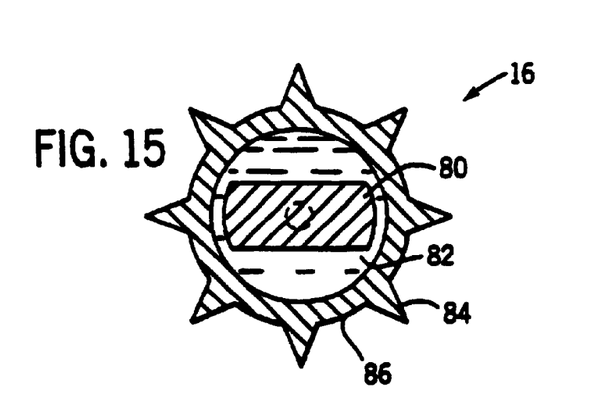
FIG. 15 is a cross sectional view of a transducer of FIG. 1 having a spiked outer collar for penetration of bark and or for better coupling with the wooden member.

Referring momentarily to FIG. 15, in a preferred embodiment, the ultrasonic transducers 16 includes a transducer element 80 held in a coupling fluid such as oil 82 as contained by the inner surface of a rotating wheel 86 as is done in the commercially available transducers 16 described above. In distinction, however, the outer surface of the wheel provides a series of radially extending spikes 84 whose sharpened tips may embed themselves in the wooden member to better couple ultrasonic energy into and out of the wooden member and to penetrate bark and the like which generally inhibit the transmission of ultrasonic energy. The sharpened tips of the spikes concentrate pressure to provide improved penetration.

Figure 2:
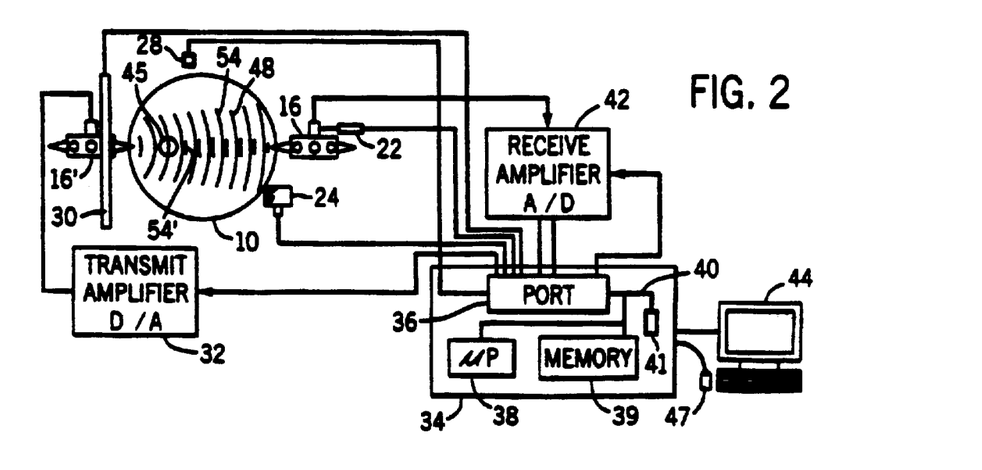
FIG. 2 is a block diagram showing the transducers and wooden member of FIG. 1 together with associated processing circuitry for generating and receiving ultrasonic signals and processing the same including an electronic computer having a standard computer monitor and keyboard.

As shown in FIG. 2, the invention operates under the control of a standard desk top computer 34 such as a so called "Wintel" computer using the Windows operating system and an Intel 133 MHz Pentium processor chip set. Computer 34 includes a port 36, a processor 38, and electronic memory 39 of a type familiar to those of ordinary skill in the art, all interconnected by an internal bus 40. The port 36 accepts input digital signals from devices outside the computer 34 and provides output digital signals to devices outside the computer as generated by execution of a stored program as will be described. The principal output signal generated is a digitized ultrasonic pulse waveform, which is communicated through the port 36 to an amplifier/D to A converter 32. The amplifier/D to A converter 32 converts the digitized ultrasonic pulse waveform to a high power analog electrical signal that is output to one 'transmitting' ultrasonic transducer 16 to drive the transmitting ultrasonic transducer 16' to produce a predetermined broadband ultrasonic pulse of predetermined phase and frequency content, in the preferred embodiment having a center frequency of substantially 80 kHz. It will be understood to those of ordinary skill in the art that other frequencies may also be used.

The port 36 also receives inputs from receiving transducer 16 detecting the ultrasonic waveform after it has passed through the wooden member 10 as pre-processed by a gain-controllable amplifier/A to D converter 42. Gain-controllable amplifier/A to D converter 42 preferably provides at least eight-bits of resolution and a sampling speed of at least 2.5 times the center frequency of the ultrasonic waveform being transmitted. The gain-controllable amplifier/A to D converter 42 provides for amplification over a fifty dB range as controlled by the computer 34.

Port 36 also receives inputs from the proximity sensors 28, the linear position sensor 22, the encoder/roller assembly 24, and the sensor array 30 so as to make their measurements available to the computer 34. A separate port 41 connects the computer 34 to the standard computer monitor 44 and keyboard/mouse 47.

During operation of the apparatus of the present invention, the computer 34 executes a stored program held in memory 39 to cause the transmission of the broadband ultrasonic pulse from transducer 16' to transducer 16. The computer 34 then collects and processes the data from transducer 16 receiving the ultrasound pulse after transmission through and modification by the wooden member 10, as well as inputs from the other sensors to evaluate the wooden member 10. The rate at which the computer controls the amplifier/D to A converter 32 to transmit the broadband pulse is determined by the desired spatial sampling rate, and the speed of the wooden member 10 as it is moved into the translation direction 12. In one embodiment, the computer controls the amplifier/D to A converter 32 so as to transmit the broadband pulse thirty-two times per second providing a sampling of the wooden member 10 as it is moved in the translation direction 12, every 0.12 inches, assuming a twenty foot per minute speed of the wooden member 10.

The effective aperture of the transmitting and receiving ultrasonic transducers 16' and 16, and the sound transmission properties of the wooden member 10 define an effective beam 48 through the wooden member 10 along which measurements will be made. The wooden member 10 may include a localized anomaly 45, such as a knot or check, which may or may not significantly affect the overall strength of the wooden member 10. In the case shown, the localized anomaly 45 has a size substantially less than the width of the beam 48. Accordingly, it will be expected that a portion along path 54 of the beam 48 will miss the localized anomaly entirely, significantly reducing the contribution of the localized anomaly 45 on any modification of the beam 48 by the wooden member. Thus an interference occurs between the sound of path 54' traveling though the anomaly 45 and the sound of path 54 traveling through unaffected wood. Alternatively, a narrow beam may be used such as will be substantially completely intercepted by the anomaly. Further, for the case in which the wooden member is a board, and the ultrasound transducers are disposed on either edge, the anomaly may encompass the entire lateral dimension of the wooden member, completely intercepting the ultrasound beam regardless of the beam width. In either case, signals may be compared against a standard signal taken at an earlier or later time of unaffected wood or derived from a model of unaffected wood.

Figure 3:
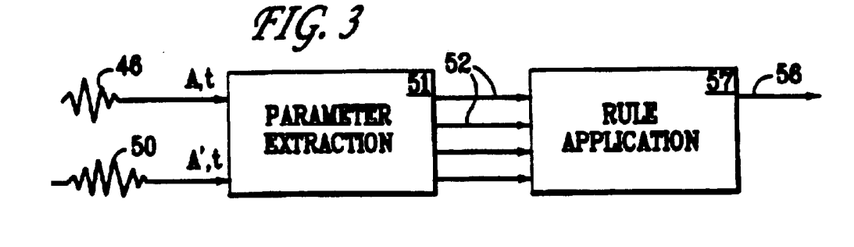
FIG. 3 is a schematic representation of a processing program executed by the computer of FIG. 2 receiving an ultrasonic waveform through the wooden member and comparing it to a transmitted ultrasonic waveform passing through a standard material to produce multiple measurement parameters which may be combined to detect localized anomalies.
Figure 17:
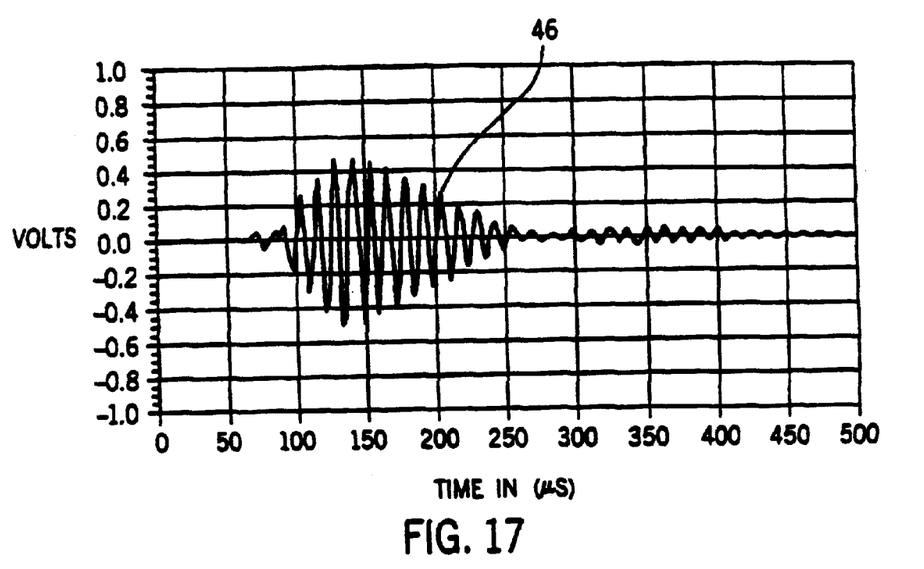
FIG. 17 is a graph of signal voltage vs. time for a representative waveform of FIG. 3 passing through the standard material.
Figure 18:
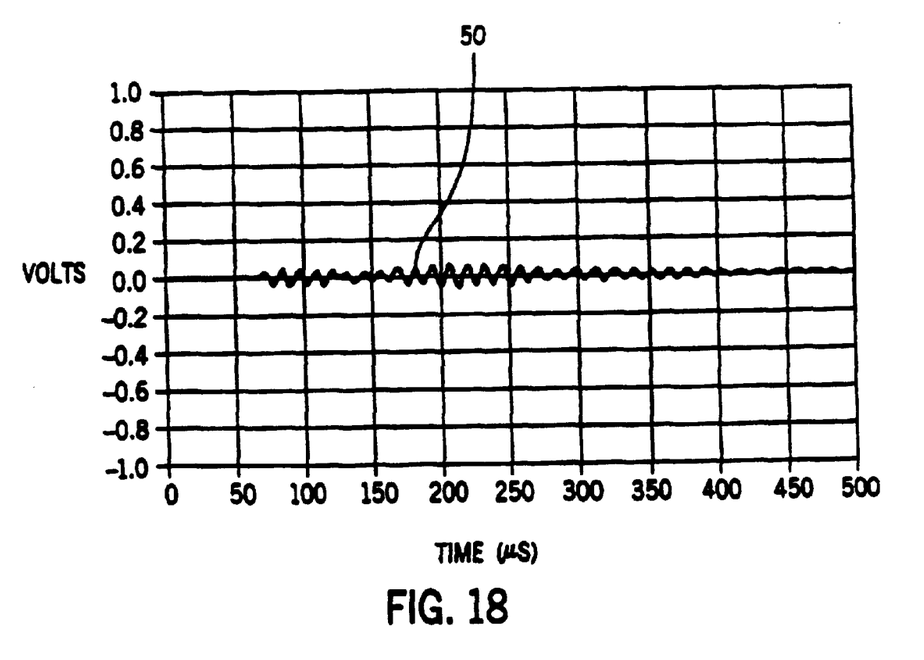
FIG. 18 is a graph of signal voltage vs. time for a representative waveform of FIG. 3 passing through the wooden member being evaluated.

As shown in FIGS. 3 and 17, the standard waveform 46 derives from a digitized version stored within the memory 39 as ordered pairs of amplitude values (A) having distinct times values (t). The standard waveform 46 represents a waveform received through a standard material without localized anomalies, such as clear wood or plastic. The received waveform 50, (shown in FIG. 18) being an actual measurement of the wooden member 10, may be similarly stored in memory 39 as a set of received amplitude values (A') at later time values (t), the delay resulting generally from the transit time in the passage of the waveform through the wooden member 10.

Figures 5, 6, 7:
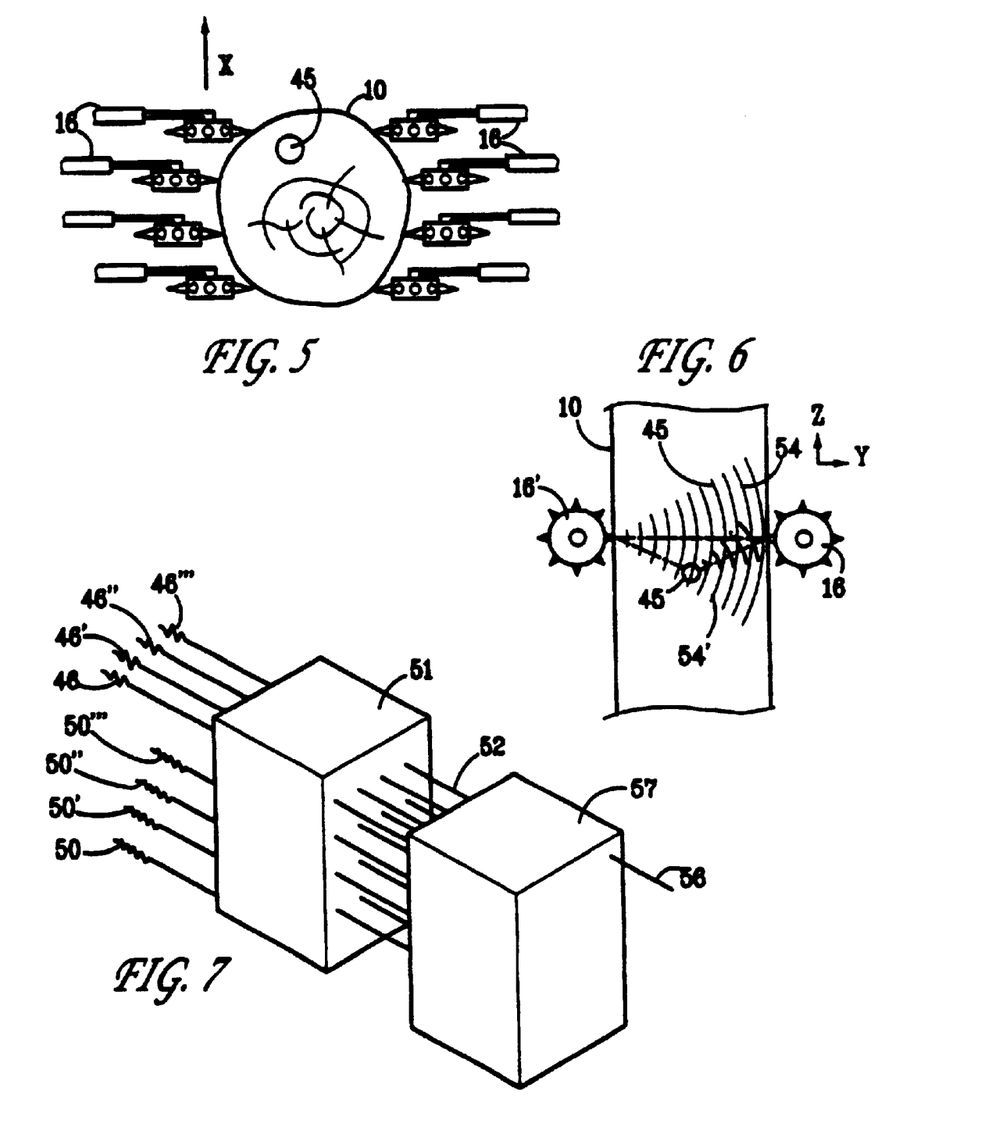
FIG. 5 is an alternative embodiment of the transducer assembly of FIG. 1 showing multiple transducers positioned in an array along an x-axis across the grain of the wooden member to provide improved localization of the internal anomalies of the wooden members.
FIG. 6 shows a plan view in cross section of the wooden member and transducers of FIG. 1.
FIG. 7 is a figure similar to that of FIG. 3 showing the multiparametric measurement of FIG. 3 applied to the additional dimension of x or z (the translation axis) in the embodiments of FIGS. 5 and 6 to provide a more robust measurement of localized anomalies.

As shown in FIGS. 3 and 6, the two waveforms of the standard waveform 46 and received waveform 50 are then analyzed according to a number of different techniques to produce parameters 52. Specifically, and referring again to FIG. 2, the present inventors have recognized that even though the localized anomaly 45 may be relatively small in comparison to the total width of the ultrasound beam 48, a portion of the beam 48 passing along a path 54 through the localized anomaly 45 modifies the remaining portion of the beam 48 passing along a path 54' outside the localized anomaly 45, the resulting interference modifying the received waveform 50 in phase and amplitude or other characteristics in a manner that may be detected and analyzed. Similarly, the ultrasound beam 48 may only pass through a portion of the localized anomaly 45, irrespective of the size of the localized anomaly 45, depending upon the orientation of the ultrasound beam 48, which also results in interference modifying the received waveform 50. This analysis involves extracting various parameters 52 from the received waveform 50, each parameter 52 selected to detect a distortion in the received waveform 50 caused by interference between waveforms on different paths 54 and 54'.

A basic parameter is that of the spreading of the received waveform 50 with respect to the standard waveform 46 caused by variation in the effective path lengths 54 and 54' (caused both by differences in path length and differences in sound speed) such as tends to spread the received waveform 50 in time. Pulse length is defined in the preferred embodiment as 1.25 times the time required for the received wave energy integral to rise from ten percent to ninety percent of its final value. Wave energy as understood in the art is determined by the formula:

$$WE = \int v^2(t)dt \quad (1)$$

where v is the voltage produced by the transducer 16 and t is time. The pulse length of the received waveform 50 is compared against the pulse length of the standard waveform 46 calculated in a similar manner to produce the relevant parameter.

The effect of the localized anomaly 45 may also change the insertion loss between the two transducers 16' and 16. This forms a second parameter of the measurement and is defined as the ratio of the energy received by the transducer 16' to the energy input into the wooden member 10 by the transducer 16 according to the following formula:

$$IL(db) = 10\log[E_r/E_t]G \quad (2)$$

where $E_r$ is the received energy $E_t$ is the transmitted energy and G is the receiver gain as may be programmed as described above. Insertion loss may be further compared to a reference value taken through a standard of known acoustic properties such as a clear wooden members or a standard reference material such as water or homogenous plastic block. Insertion loss may be further compared as a function of the distance that the ultrasound wave travels through the wooden member (using a width measurement from the linear position sensor 22), expressed in Decibels per inch (or decibels per centimeter).

A third parameter may be the time of flight of the pulse determined by a correlation of the standard and received waveforms 46 and 50 such as may provide an indication of the overall qualities of the wooden member 10 outside of the localized anomaly 45. This time of flight value may alternatively be divided by a width measurement from the linear position sensor 22 to produce a sound velocity measurement.

A fourth parameter uses a deconvolution of the received waveform 50 by the standard waveform 46 which may be expressed mathematically as either:

$$FFT^{-1}\left[\frac{CrossPower(Reference,\ Unknown)}{Power\ Spectrum\ (Unknown)}\right] \quad (3)$$

or $$FFT^{-1}\left[\frac{FFT\ (Unknown)}{FFT\ (Reference)}\right] \quad (4)$$

where FFT and $FFT^{-1}$ are the Fourier transform and the inverse Fourier transform, respectively, and wherein the Unknown is signal through the wooden member 10 and the Reference is a signal through a reference standard of known acoustic properties. This deconvolution allows the detection of multiple signal paths through the wooden member 10 whose variation may indicate the presence of a localized anomaly 45 which creates effectively a new path through the wooden member 10. Other methods such as homomorphic filtering known to those of skill in the art may be used for the same purpose.

Figure 4:
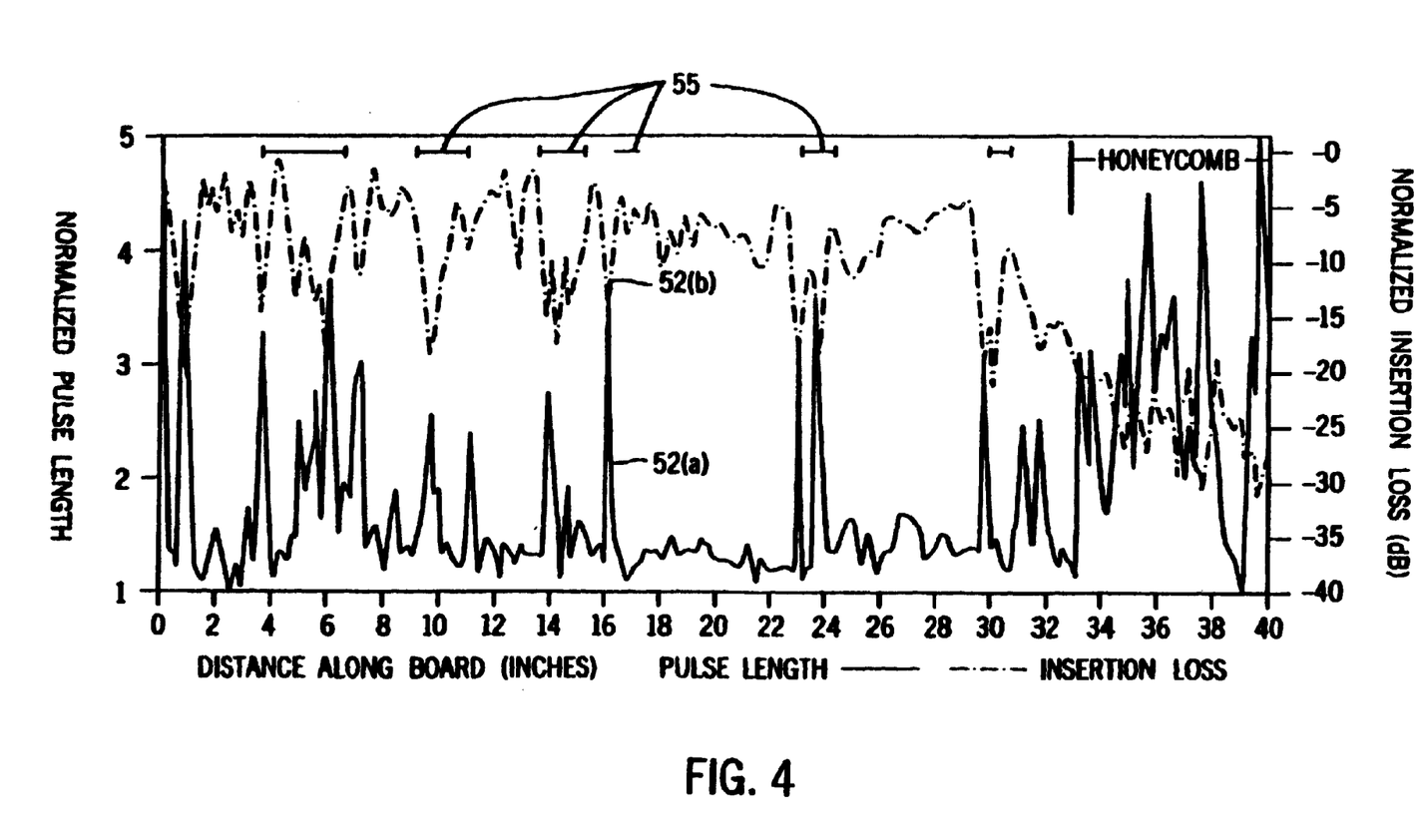
FIG. 4 is a graph of two such parameters, specifically pulse length and insertion loss (defined below), plotted against distance along the translation axis showing the position of local anomalies evident by examination of these two parameters.

As shown in FIGS. 3 and 4, two or more parameters may be compared over the length of the wooden member 10 along the translation direction 12 to detect localized anomalies 45. In the example of FIG. 4, peaks in pulse length 52(*a*) and troughs in insertion loss 52(*b*) correlate to regions 55 in which localized anomalies 45 are found. Accordingly, an empirically derived rule may be developed by testing each of pulse length 52(*a*) and 52(*b*) against a threshold and logically ANDing the test outcomes together to produce an output indicating a localized anomaly 45. The rule may be implemented by explicit rules programmed into the computer 34 or may be performed by artificial intelligence techniques such as neural networks or fuzzy logic known in the art. Such rules are shown by rule application block 57 and may combine two or more parameters 52.

The benefits of multiple parameter measurement can be further seen in Table I below for various types of wood conditions.

TABLE I

| Parameter | Normal | Wetwood | Knot | Honeycomb |
|---|---|---|---|---|
| Insertion Loss (dB) | −50 | −70 | −66 | −78 |
| Pulse Length (µs) | 110 | 235 | 244 | 239 |
| Time of Flight | 80 | 90 | 80 | 96 |

Figure 16:
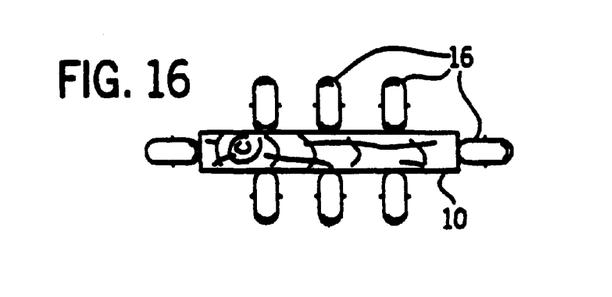
FIG. 16 is a view similar to that of FIG. 5 showing transducers positioned along both the x and y axes about a board.

As shown in FIG. 5, an array of ultrasonic transducers 16 and 16' may be positioned at varying x-axis locations on the side of the wooden member 10 pairs opposed along different axes both radial and tangential to the wooden member 10 across the grain of the wooden member 10 to provide a different parametric reading for each x-axis location. These transducer arrays provide additional spatial information about the location of a localized anomaly 45 in the x-axis direction. In an alternative embodiment shown in FIG. 16, transducers 16 may be placed arrayed along either or both of the x and y-axis to locate the localized anomaly 45 with respect to the x and y-axes. This embodiment is particularly useful for grading lumber as to strength where the location of a knot, as opposed simply to its existence, is important as to its effect on strength. Strength grading can be used to determine the location of pieces of lumber in the final product, for example a pallet, where stronger pieces of lumber are used for the core of the pallet and the weaker pieces of lumber are used for the planking that serves merely to provide the pallet surface. In the embodiment of FIG. 16, individual top transducers 16 may be excited while readings are taken at all bottom transducers 16 so as to obtain measurements along four simultaneous axes for each excitation and reading along sixteen axes for all four top transducers 16. These multiple readings may be used to triangulate the location of the anomaly.

As shown in FIG. 7, the parameter extraction block 51 for any of these multiple measurement embodiments of FIGS. 6 and 7 will receive a two dimensional array of standard waveforms 46–46" and received waveforms 50–50'". Each corresponding standard and received waveform 46 and 50 may be compared as described with respect to FIG. 3 but additional cross combinations of the various waveforms may also be used to produce new effective particular parameters such as spatial rates of change of the parameters in the x or z direction.

As before, these parameters 52 may be provided by rule application block 57 to produce an output 56 providing an identification of localized anomalies 45 and further providing additional spatial location of localized anomalies 45 in the x-axis or y-axis. Specifically, the x- and y- axis positions of localized anomalies 45 may be determined from the parameters derived from the location of individual transducer pair satisfying the rule of rule block 57 in the same way that the z-axis position is determined as described with respect to FIG. 4. In this way, a map of the spatial location of localized anomalies 45 for the entire wooden member 10 may be developed.

Using this map, decisions about length of cuts of the wooden member 10 across the z-axis (to remove localized anomalies 45 from boards) may be augmented with decisions about rip cuts of the wooden member 10 along the z-axis so as to maximize the value of the cut wood by moving localized anomalies 45 among boards.

Figure 8:
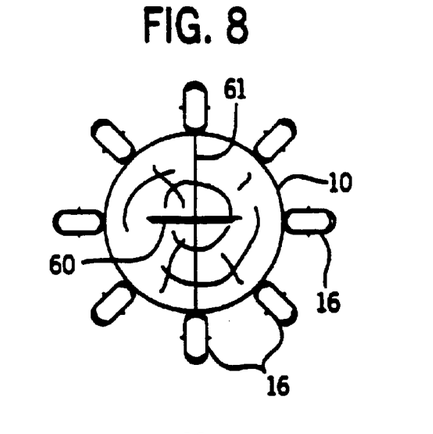
FIG. 8 is a figure similar to FIG. 5 showing transducers arrayed radially around the circumference of the wooden member such as may be useful for the detection of internal splits or checks.

As shown in FIG. 8 a set of transducers 16 may be arrayed about the periphery of the wooden member 10 so that the plane of the wheels of each transducer 16 includes the z-axis and extends radially therefrom so as to provide axis 61 between pairs of transducers 16 that extend radially through the wooden member 10. This configuration may be used to identify splits 60 within the wooden member 10 such as have a varying cross section depending on the radial direction along which they are viewed. Thus such splits 60 may be localized to lie narrowly along one radial direction while being relatively broad in another radial direction.

Figure 9:
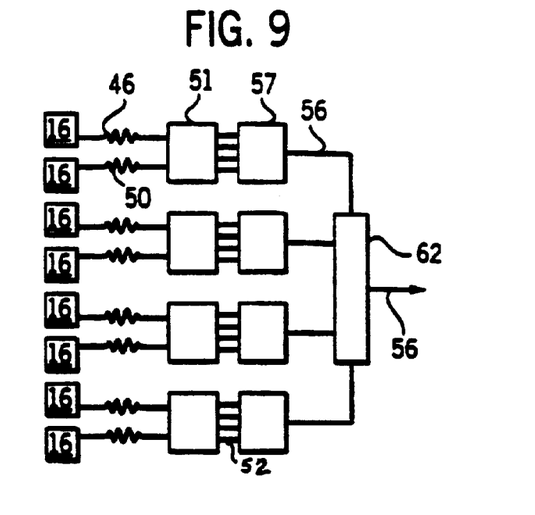
FIG. 9 is a block diagram similar to that of FIG. 3 showing the repetition of the element of FIG. 3 for each of the transducers of FIG. 8 and collected by a parameter extraction block identifying an orientation of a split.

As shown in FIG. 9, each opposed pair of transducers 16 is connected to a parameter extraction block 51 (as described above) so as to provide a plurality of parameters 52 associated with different radial angles. Each parameter extraction block 51 is associated with a rule application block 57 to produce an output 56 for each radial angle. The outputs may be compared by a parameter extraction block 62 to identify the plane of the split as it crosses the x-y axis. In one embodiment, the parameter extraction block 62 may be a simple magnitude comparator. Generally the radial angle associated with the greatest insertion loss will be perpendicular to the plane of the split 60.

EXAMPLE I

Measurements were made of a log prior to cutting ("undisturbed") and after cutting, at various angles with respect to a split as indicated in the following Table II. The measurements were time of flight (TOF) as detected by an amplitude threshold (TOFa) or an energy threshold (TOFe). Pulse length (PL) using IEC standard 1157 and insertion loss (IL) were also measured.

TABLE II

| Angle with Respect to Split | TOFe | TOFa | PL | IL |
| --- | --- | --- | --- | --- |
| 90° | 501 | 449.9 | 306.27 | −89.76 |
| 45° | 553.8 | 434.3 | 290.87 | −81.85 |
| 0° | 220.5 | 146.9 | 175.42 | −69.26 |
| Undisturbed | 193.1 | 146.2 | 172 | −73.93 |

The zero degree reading corresponds closely to the undisturbed reading; however, the 45° and 90° readings differ significantly from the baseline readings. The changes in pulse length and times of flight are by factors of 1.5 to 2.5; the insertion loss change is over 20 db, or 100 to 1.

Table III below provides successive readings of the same parameters taken along the log at increasing distances from the cut face.

TABLE III

| Distance from Cut (mm) | TOFe | TOFa | PL | IL |
| --- | --- | --- | --- | --- |
| at cut face | 503.1 | 331.8 | 407.05 | −93.55 |
| 220 | 239 | 120.8 | 435 | −95 |
| 240 | 221 | 141 | 425 | −93.1 |
| 280 | 210 | 142.2 | 176 | −80.98 |
| 300 | 187 | 138.9 | 158 | −70.7 |
| 330 | 181 | 139.5 | 140.5 | −71.66 |
| Undisturbed | 177.5 | 142 | 147 | −70.5 |

In this case the three parameters change independently. The times of flight change quickly as a function of distance from the cut face because any sound transmission around the cut will reach the receiver as quickly as in the undisturbed case. However, the pulse length and insertion loss indicate reduced amplitude and significant pulse distortion from multipath signals. At 280 mm from the cut face, the pulse length has reduced to near its original values indicating that the signal is predominantly a direct path from transmitter to receiver. The remaining split has caused a reduction in signal strength, but has not affected the other parameters. Finally at 300 mm and beyond, the signals have returned to their original values.

Figure 10:
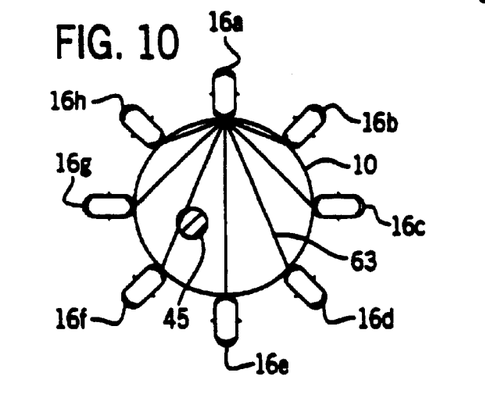
FIG. 10 is a figure similar to that of FIG. 8 showing the use of the transducer assembly of FIG. 8 for tomographic analysis of the internal structure of the wooden member.

As shown in FIG. 10, in a alternative embodiment to the embodiment of FIG. 7, the consideration of the cross terms of the various standard and received waveforms 46 and 50 and their deduced parameters may be realized with a tomographic reconstruction. In this tomographic reconstruction, each ultrasonic transducer 16, for example, ultrasonic transducer 16(a) may sequentially serve as a source of ultrasonic energy to be received by each of the other ultrasonic transducers (b) through (h). Relatively narrow effective beam widths along projection lines 63 may be obtained in this manner. The standard waveform 46 of the selected ultrasonic transducer 16a may be compared pairwise to the received ultrasonic waveforms 50 of each of the ultrasonic transducers 16b–h to produce a separate parameter measurement. The parameters measured may be any of those previously described or other similar measurements.

Figure 11:
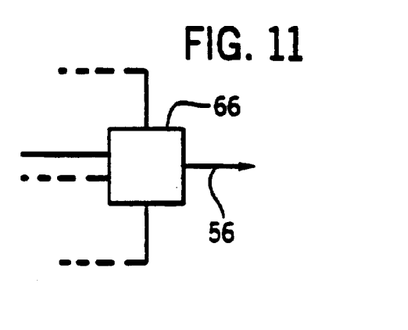
FIG. 11 is a fragmentary view of FIG. 9 showing a tomographic back projection block used to replace the parameter extraction block of FIG. 9 when the assembly of FIG. 8 is used for tomographic analysis.

As shown in FIG. 11, the parameters themselves or rule based combinations of parameters derived from measurements along ones of different projection lines 63 are then provided to a tomographic reconstructor 66 such as is known in the art of x-ray tomography to provide an image of a cross sectional cut through the wooden member 10 in the x-y plane. Such a tomographic reconstructor 66 may use a fan beam, filtered back projection algorithm known in the art. This x-y mapping may augment z-axis information obtained by taking multiple projections at different z-axis locations along the wooden member 10 allowing for multidimensional optimization of the cutting of the wooden members.

Figure 12:
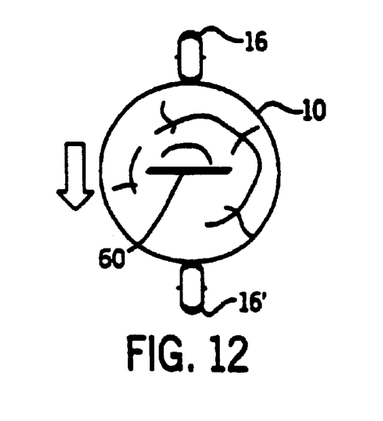
FIG. 12 is a figure similar to that of FIGS. 8 and 10 showing the wooden member in cross section along the x-y plane with a single pair of transducers positioned for the detection of dynamic splits caused by a sawing operation.
Figure 13:
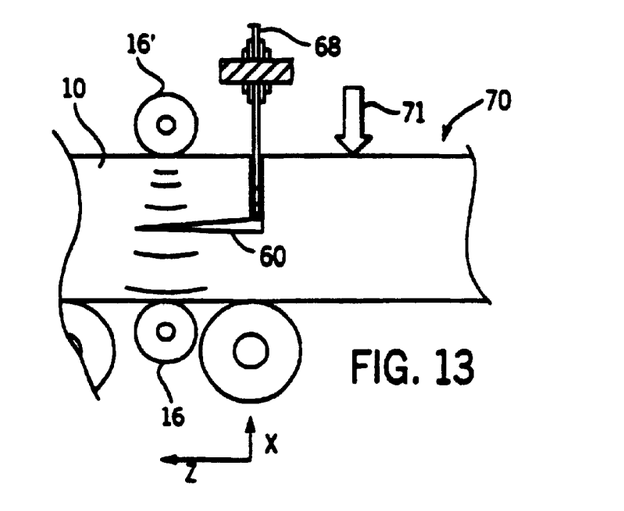
FIG. 13 is a view of the wooden member of FIG. 12 along the x-z plane showing a development of a dynamic split with respect to the transducers of FIG. 12 during the cutting operation caused by the cantilevered weight of the end of the wooden member.

As shown in, FIG. 12, in a variation on the embodiment of FIG. 8, a single pair of transducers 16 and 16' may be placed in vertical opposition about the wooden member to detect dynamic splits 60 occurring in a horizontal plane as caused by a cutting of the wooden member 10. As shown in FIG. 13, such splits may occur when a cut by a saw 68 is made in the x-y plane part way through the wooden member 10 upon which the cantilevered weight of an end 70 of the wooden member 10 exert a downward force 71 causing the split 60. Such dynamic splits caused by force 71 may close after the cut is complete but may still be identified by the technique of FIG. 8. However, by using a concurrent transmission of ultrasonic energy adjacent to the cut line of the saw 68 on the supported side of the wooden member 10 during the cutting process, the split may be detected as it occurs and decisions about the board made in real-time. Again multiple transducers displaced as shown in FIG. 6 may be used to characterize the depth of the split. Appropriate bandpass and time window filtering and choice of measurement parameters may be used to permit the split to be detected without interference from both the electronic and vibrational noise of the cut of the saw 68. Knowing that the split 60 is occurring may allow the saw operator to adjust the sawing procedure to reduce the incidence of splitting. Further knowing the depth of the split with a disposition of the transducers (not shown) along the z axis or the length of the wooden member may allow the operator to adjust the length of the sawn wooden member 10 such that a desired length of un-split wood is produced.

Figure 14:
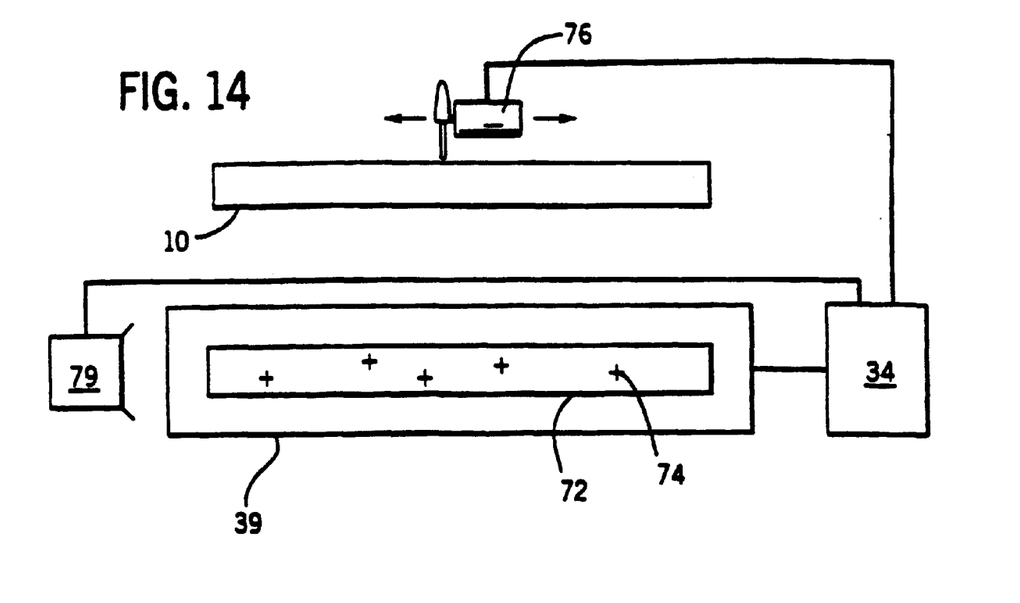
FIG. 14 is a schematic representation of a computer controlled cutoff saw suitable for cutting wooden members as characterized by the present invention so as to optimize usage of wooden members based on the location of identified anomalies.

As shown in FIG. 14, the present invention provides in the memory 39 of the computer 34 a map 72 of the wooden member 10 indicating sites 74 of local anomalies 45 identified to spatial locations within the wooden member 10. The computer 34 reading the map 72 and executing commercially available optimization routines may control a computer movable saw 76 as are understood in the art to make appropriate cross cuts and rip cuts of the wooden members 10 so as to optimize the value of the wooden members 10 in the commercial market. Alternatively or in addition, the computer 34 may provide output to a commercial sorting machine to mark or direct the wooden member as to strength or grade thereby allowing more efficient use of lumbers of different strengths and in particular better use of lower grade lumbers so as to waste less wood.

It will be also understood that the detection method of the present invention may be combined with conventional visual or laser type knot and split detection equipment to augment those systems to obtain more robust detection or greater detection range.

Figure 19:
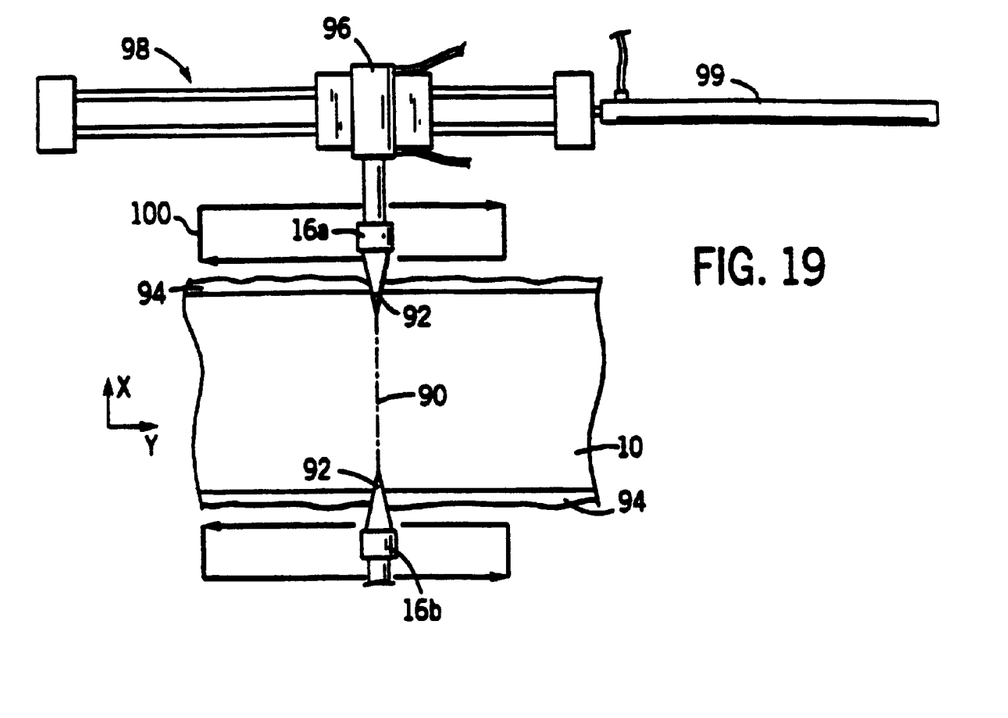
FIG. 19 is a view similar to FIG. 13 showing an alternative embodiment of the transducers using spiked transducers and a plunge translate and retract mechanism.

As shown in FIG. 19, in an alternative embodiment, transducer 16a and 16b providing opposed transmitting and receiving ultrasonic transducers aligned along an axis 90 through wooden member 10 may have spike portions 92 presenting a sharpened tip that may be plunged into the wood member 10 along axis 90 thereby passing through an outer layer of bark 94. Each of transducers 16a and 16b may be mounted to a bidirectional hydraulic or air cylinder 96 (shown only for transducer 16a) which when activated in a first direction may move the transducers 16 toward the wooden member 10 and when activated in a second direction may retract it away from the wooden member 10.

The cylinder 96 may be mounted on a z-axis carriage 98 allowing it to move with motion of the wooden member 10 in the z direction for continuous processing and measurement of the wooden member 10. At the conclusion of the translation of the log in the z direction, the transducers 16 may be retracted and a second hydraulic cylinder 99 may be used to advance the carriage 98 back along the z-axis whereupon the transducers 16 may be reinserted into the wooden member 10. In this way, the transducer 16a and 16b follow a rectangular cycle 100 permitting continuous motion of the wooden member 10.

Figure 20:
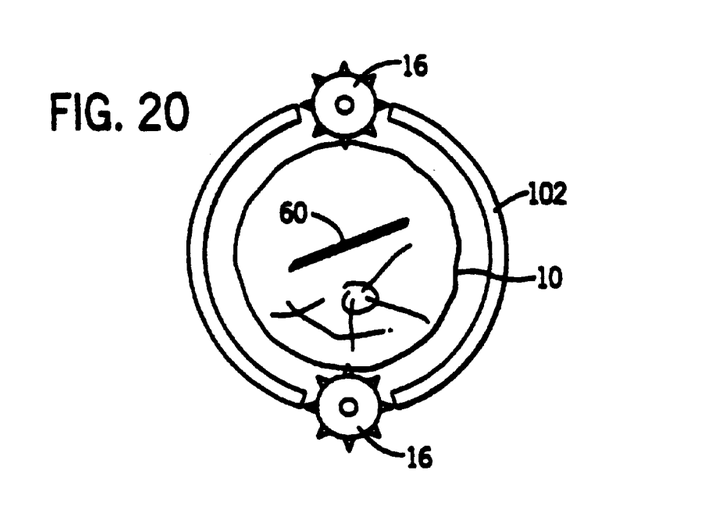
FIG. 20 is a figure similar to that of FIG. 12 showing mounting of wheeled transducers for rotational translation about the wood.

As shown in FIG. 20, in yet another embodiment, transducers 16 may be mounted on a carriage 102 extending about the wooden member 10 in the x-y plane allowing them to be rotated orbitally about the Z-axis of the wooden member 10 so as to obtain measurements along a number of different radial x-y paths through the wooden member 10 for use in detection of split 60 or for tomographic-type measurements. The transducers may be retracted to allow z axis motion of the wooden member 10 or the transducers 16 may be canted so as to allow them to roll in a helical path with respect to the wooden member 10 as the wooden member 10 moves along the Z-axis for substantially continuous processing. The carriage 102 thus provides a physical scanning means that is an alternative to the extraction block 62 which provides an electronic scanning.

The above description has been that of a preferred embodiment of the present invention, it will occur to those that practice the art that many modifications may be made without departing from the spirit and scope of the invention. In order to apprise the public of the various embodiments that may fall within the scope of the invention, the following claims are made.

What is claimed is:

1. A method of detecting anomalies in a wooden member, comprising the steps of:

transmitting an ultrasonic wave of known characteristics from a first transducer through said wooden member; and receiving said ultrasonic wave at two or more transducers.

2. The method of claim 1, further comprising the step of comparing at least one characteristic of said ultrasonic wave received at said two or more transducers with at least one corresponding characteristic of said ultrasonic wave transmitted by said first transducer.

3. The method of claim 2, further comprising the step of identifying abnormalities in said wooden member based on said step of comparing.

4. The method of claim 3, further comprising the step of grading said wooden member based on said abnormalities.

5. The method of claim 1, further comprising the step of determining a standard set of measurements by transmitting said ultrasonic wave from said first transducer through an acceptable wooden member.

6. The method of claim 5, further comprising the step of comparing at least one measurement of said standard set of measurements with at least one corresponding measurement of said wooden member.

7. The method of claim 6, further comprising the step of identifying abnormalities in said wooden member based on said step of comparing.

8. The method of claim 7, further comprising the step of grading said wooden member based on said abnormalities.

9. A method of detecting anomalies in a wooden member, comprising the steps of:

transmitting a plurality of ultrasonic waves of known characteristics from a first transducer through said wooden member; and receiving said ultrasonic waves with at least two transducers.

10. The method of claim 9, wherein the step of transmitting further comprises the step of transmitting a different ultrasonic wave to each of said two or more transducers in sequence.

11. The method of claim 9, wherein the step of transmitting further comprises the step of tomographically transmitting said ultrasonic waves such that said first transducer may sequentially transmit said ultrasonic waves to said two or more ultrasonic transducers.

12. The method of claim 9, wherein the step of transmitting further comprises the step of transmitting said plurality of ultrasonic waves such that said two or more transducers each receive each of said plurality of ultrasonic waves.

13. The method of claim 9, further comprising the step of comparing at least one characteristic of said ultrasonic waves received at said two or more transducers with at least one corresponding characteristic of said ultrasonic waves transmitted by said first transducer.

14. The method of claim 13, further comprising the step of identifying abnormalities in said wooden member based on said step of comparing.

15. The method of claim 14, further comprising the step of grading said wooden member based on said abnormalities.

16. The method of claim 9, wherein said first transducer is different than said two or more transducers.

17. A system for detecting anomalies in a wooden member, comprising:

a first transducer for transmitting an ultrasonic wave of known characteristics through said wooden member;

two or more transducers for receiving said ultrasonic wave;

a computer-based device in communication with said first transducer and said two or more transducers for comparing at least one characteristic of said ultrasonic waves received at said two or more transducers with at least one corresponding characteristic of said ultrasonic waves transmitted by said first transducer.

18. The system of claim 17, further comprising a display in communication with said computer-based device for identifying abnormalities based on said comparison.

19. The system of claim 17, wherein said computer-based device determines a grade for said wooden member based on said identified abnormalities.

20. The system of claim 17, wherein said computer-based device stores a standard set of measurements, wherein said standard set of measurements represent the transmission of said ultrasonic waves of known characteristics from said first transducer through an acceptable wooden member.

21. The system of claim 17, wherein said first transducer is located in a first array of transducers, and wherein said two or more transducers are located in a second array of transducers.

* * * * *